United States Patent [19]

Kido et al.

[11] Patent Number: 5,770,233
[45] Date of Patent: Jun. 23, 1998

[54] CONTAINER FILLED WITH INFUSION LIQUIDS AND INFUSION PREPARATION

[75] Inventors: Takae Kido; Shigeo Ii; Shun-ichi Abe; Kazumasa Yokoyama, all of Osaka, Japan

[73] Assignee: The Green Cross Corporation, Osaka, Japan

[21] Appl. No.: 437,330

[22] Filed: Apr. 21, 1995

Related U.S. Application Data

[63] Continuation-in-part of PCT/JP93/01521, Oct. 21, 1993.

[30] Foreign Application Priority Data

Oct. 22, 1992 [JP] Japan ..................................... 4-309249

[51] Int. Cl.$^6$ ............................... A61K 9/00; A61K 9/08; A61K 33/00; A61K 31/70; A61K 31/59; A61K 31/595; A61K 31/34; A61J 1/00

[52] U.S. Cl. .......................... 424/641; 424/400; 424/600; 424/639; 424/646; 424/653; 424/654; 424/655; 424/673; 424/677; 424/682; 424/702; 424/722; 514/23; 514/53; 514/54; 514/167; 514/168; 514/249; 514/251; 514/356; 514/387; 514/400; 514/419; 514/423; 514/458; 514/474; 514/547; 514/556; 514/561; 514/562; 514/563; 514/564; 514/565; 514/567; 514/681; 514/725; 514/904; 514/905

[58] Field of Search ..................................... 424/600, 639, 424/641, 646, 653, 654, 655, 673, 682, 702, 400, 722; 514/23, 53, 54, 167, 168, 249, 251, 356, 387, 400, 419, 423, 458, 474, 547, 556, 561, 562–565, 567, 681, 725, 904, 905

[56] References Cited

U.S. PATENT DOCUMENTS

| | | | |
|---|---|---|---|
| 4,005,190 | 1/1977 | Mader et al. | 424/127 |
| 5,560,403 | 10/1996 | Balteau et al. | 141/9 |
| 5,626,880 | 5/1997 | Inoue et al. | 424/489 |
| 5,674,527 | 10/1997 | Inoue et al. | 424/450 |

FOREIGN PATENT DOCUMENTS

| | | |
|---|---|---|
| 0 510 687 | 10/1992 | European Pat. Off. . |
| 58-162515 | 9/1982 | Japan . |
| 58-162517 | 9/1983 | Japan . |
| 61-058560 | 3/1986 | Japan . |
| 62-135421 | 6/1987 | Japan . |

OTHER PUBLICATIONS

DerwentAbstract N89–244721, abstracting JP 1–240469, 1989.

Chemical Abstracts 99:146124J, 1983.

Chemical Abstracts 69:89709h (1968).

*Primary Examiner*—John Pak
*Attorney, Agent, or Firm*—Sughrue, Mion, Zinn, Macpeak & Seas, PLLC

[57] ABSTRACT

An object of the present invention is to provide an infusion preparation set (a container filled with infusion liquids) useful for preparation of an infusion liquid containing sugars, amino acids, electrolytes, a fat emulsion and vitamins. The present invention is constituted by the use of a container having two compartments which are separated from each other by a separation means, which contains an infusion liquid comprising a fat emulsion, sugars, fat-soluble vitamins and specified water-soluble vitamins in the first compartment and an infusion liquid comprising amino acids, electrolytes and other specified water-soluble vitamins in the second compartment. An infusion preparation containing sugars, amino acids, electrolytes, a fat emulsion and vitamins can be obtained easily and aseptically upon use, by simply removing a separation means and mixing the infusion liquids included in the first and second compartments. Further, the components of the infusion liquids included in each compartment have good stability.

3 Claims, 3 Drawing Sheets

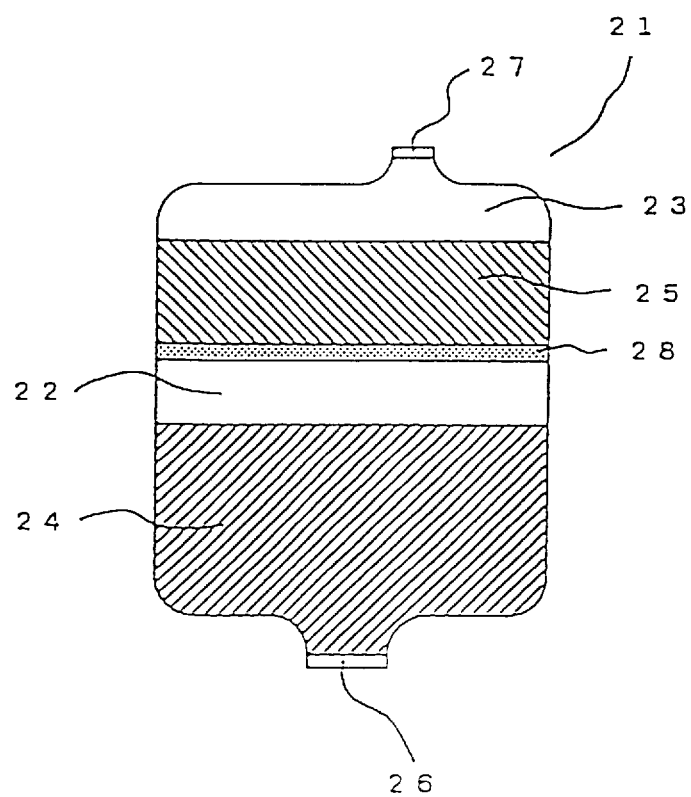

CONTAINER FILLED WITH INFUSION LIQUIDS AND INFUSION PREPARATION

CROSS REFERENCE TO RELATED APPLICATIONS

This is a continuation-in-part application of PCT Application No. PCT/JP93/01521, filed Oct. 21, 1993.

TECHNICAL FIELD

This invention relates to infusion preparations which comprise a fat emulsion, sugars, amino acids, electrolytes and vitamins, to a container filled with infusion liquids for use in making said infusion preparations and infusion liquids. More specifically, the invention relates to (1) an infusion preparation comprising a fat emulsion, sugars and specific vitamins, (2) an infusion preparation comprising amino acids, electrolytes and other vitamins, (3) a container filled with infusion preparations in which the above infusion preparations (1) and (2) are contained in the respective compartments, and (4) an infusion preparation prepared by mixing infusion liquids contained in the respective compartments.

BACKGROUND ART

Intravenous infusion is carried out for the purpose of supplying nutrients to maintain a patient's life when oral or nasal feeding is impossible or insufficient, when the digestion and absorption functions of the patient are in a poor state, even if such a feeding means can be carried out, or when the passage of food through the digestive tract makes the patient's condition or disease more serious. Examples of commercially available infusion preparations include a sugar intravenous infusion which contains reducing sugars and the like, amino acids and the like, an electrolyte infusion liquid which contains electrolytes and the like, a fat emulsion which contains a plant oil and the like, and a vitamin mixture. These infusion preparations are appropriately selected depending on the condition of the patient and are mixed upon use. However, mixing these preparations at the time of their use requires complex handling and, above all things, raises the problem of microbial contamination. With the aim of overcoming such problems, various infusion preparations, in which some of the aforementioned infusion liquids are mixed in advance, have been proposed. Infusion preparations which contain sugars, amino acids, electrolytes and a fat emulsion, all being essential nutrients to be supplied, are especially useful from a clinical point of view.

However, since these sugar infusion liquids, amino acid infusion liquids, electrolyte infusion liquids and fat emulsion are different from one another in terms of the conditions for their stable existence, various problems arise when they are mixed, and the mixture becomes useless in many cases.

For example, because of its unstable nature, a fat emulsion is apt to form bulky fat particles and to cause phase separation (creaming) when mixed with other infusion liquids. In particular, divalent cations contained in an electrolyte infusion liquid cause aggregation and disintegration of fat emulsion particles.

In the case of an electrolyte infusion liquid, since it contains calcium and phosphoric acid as essential components to maintain the balance of electrolytes, it is apt to form calcium phosphate by the reaction of calcium with phosphoric acid and therefore to generate turbidity and precipitation. In order to prevent the formation of turbidity and precipitation, such an electrolyte infusion liquid is usually adjusted to a low pH value (less than pH 5). When such a electrolyte infusion liquid is mixed with an amino acid infusion liquid, the pH of the mixture increases to the amino acid pH value because of the strong buffer action of amino acids, thus requiring a large quantity of acidic materials (for example, hydrochloric acid, acetic acid and the like) to keep the pH value at a low level. However, acidic materials can be used only in a limited amount because a large quantity of acid spoils the balance of the infusion components. As a consequence, the pH value of the mixture of electrolyte and amino acid infusion liquids cannot be lowered to a satisfactory level, thus resulting in the generation of turbidity and precipitation at the time of heat sterilization of the mixture.

In addition, when a mixture of an amino acid infusion liquid with a sugar infusion liquid is sterilized by heating, considerable coloring occurs due to the Maillard's reaction.

As described above, it is difficult to prepare a storable infusion preparation which contains a sugar, amino acids, electrolytes and a fat emulsion, in advance, because mixing these different types of infusion liquids or emulsions causes various problems such as precipitation, denaturation, coloring and the like. Because of these problems, a fat emulsion, a sugar infusion liquid, an amino acid infusion liquid and an electrolyte infusion liquid are ordinarily mixed upon use. As a consequence, an infusion preparation has been desired which contains sugars, amino acids, electrolytes and a fat emulsion and can be stably stored.

Under these circumstances, the present inventors have conducted intensive studies on the development of a preparation method of a stable infusion preparation which contains sugars, amino acids, electrolytes and a fat emulsion. They have found that preparations containing the above components in a certain combination can be stably stored and an infusion preparation containing sugars, amino acids, electrolytes and a fat emulsion can be easily obtained, upon use, without suffering from precipitation, denaturation, coloring and other problems. More specifically, it has been found that the above problems can be solved by putting an infusion liquid containing a fat emulsion and sugars into the first compartment of a container having two compartments which are separated by a separation means, putting an infusion liquid containing amino acids and electrolytes into its second compartment, sterilizing said container, preserving it in this state, and mixing the infusion liquids contained in the first compartment and the second compartment by removing the separation means upon use (cf. JP-A-5-31151).

It has become common to give various vitamins during treatment with total parenteral nutrition (TPN). In this instance, vitamins are added to TPN admixture upon clinical use. In order to further improve the above-described newly developed infusion preparation containing sugars, amino acids, electrolytes and a fat emulsion, it is desirable to develop TPN admixture in a more perfect form containing vitamins, in advance, thereby saving the step of adding vitamins upon clinical use.

However, vitamins are usually unstable and a certain combination of vitamins can cause decomposition of one of the vitamins or can make the liquid turbid. For example, the present inventors have found that the solution becomes turbid when folic acid is mixed with vitamin C, and that vitamin C promotes decomposition of vitamin $B_{12}$. Therefore, it is necessary to pay attention to the combination use of vitamins. Vitamins are roughly divided into two groups: a water-soluble group and a fat-soluble group. These two groups are different from each other in physicochemical properties. In particular, many water-soluble vitamins are unstable.

An investigation has been made regarding the composition of vitamins to be added into the above-described first compartment (fat+sugars) and the composition of vitamins to be added into the second compartment (amino acids +electrolytes). Further, by modifying the manner of addition, an infusion preparation containing stable vitamins can be obtained without affecting stability of sugars, amino acids, electrolytes and a fat emulsion. Thus, the present invention has been completed.

DISCLOSURE OF THE INVENTION

The container filled with infusion liquids according to the present invention, which is made for solving the above problems, comprises a first compartment containing an infusion liquid comprising a fat emulsion, sugars, vitamin C, vitamin $B_1$, vitamin $B_2$, vitamin A, vitamin D, vitamin E and vitamin K and a second compartment containing a infusion liquid comprising amino acids, electrolytes, vitamin $B_6$, vitamin $B_{12}$ and folic acid. Using this constitution, an infusion preparation comprising a fat emulsion, sugars, amino acids, electrolytes and vitamins can be prepared by removing a separation means upon use so as to open the first and second compartments to each other and thereby mix the infusion liquid contained in the first compartment and the infusion liquid contained in the second compartment. The container is thus filled with a mixed infusion liquid comprising a fat emulsion, sugar, Vitamin C, Vitamin $B_1$, Vitamin $B_2$, Vitamin A, Vitamin D, Vitamin E, Vitamin K, amino acid, electrolyte, Vitamin $B_6$, Vitamin $B_{12}$ and folic acid. The fat emulsion contained in the first compartment preferably has a mean particle diameter of 0.17 $\mu$m or less. The infusion liquid contained in the second compartment preferably contains a phosphoric ester of a polyhydric alcohol or a sugar or a salt of the ester as a source of phosphorus.

Further, the infusion preparation of the present invention includes infusion liquids contained in the first and second compartments of the above-described container filled with the infusion liquids and the infusion preparation obtained by removing a separation means of the container filled with the infusion liquids.

According to the present invention having the above-described constitution, the first compartment contains an infusion liquid comprising a fat emulsion, sugars and at least vitamin C, vitamin $B_1$, vitamin $B_2$, vitamin A, vitamin D, vitamin E and vitamin K. In the following description, for example, vitamin $B_1$ and vitamin $B_2$ are referred to as vitamins ($B_1$, $B_2$).

The fat emulsion of the present invention may be an oil-in water type emulsion which is prepared by dispersing a fat in water using an emulsifying agent. The fat emulsion may be prepared in a conventional manner, for example, by adding a fat and an emulsifying agent to water, stirring the mixture to prepare a crude emulsion and then emulsifying the crude emulsion by any commonly used means such as by a high pressure emulsification method.

Any edible fats and oils can be used as the fat source of the fat emulsion. Preferably used are one or more fats and oils selected from the group consisting of plant oils such as soybean oil, cottonseed oil, safflower oil, corn oil, coconut oil, beefsteak plant oil, perilla oil and the like; fish oils such as cod liver oil and the like; medium-chain fatty acid triglycerides such as Panacet (trade name), ODO (trade name) and the like; and chemically synthesized triglycerides such as chemically defined triglycerides including 2-linoleoyl-1,3-dioctanoyl glycerol (8L8), 2-linoleoyl-1,3-didecanoyl glycerol (10L10) and the like.

Any emulsifying agent commonly used in pharmaceutical preparations may be used in the present invention. One or more agents may be used which are preferably selected from the group consisting of egg yolk phospholipids, hydrogenated egg yolk phospholipids, soybean phospholipids, hydrogenated soybean phospholipids and nonionic surface active agents such as Pluronic F68 (trade name) and HCO-60 (trade name).

A soybean oil and egg yolk phospholipid are particularly preferred as the fat source and as the emulsifying agent, respectively, to prepare a fat emulsion.

According to the present invention, the fat emulsion may preferably be prepared so that its mean particle diameter becomes 0.17 $\mu$m or less. By controlling the particle diameter at this level, higher stability of the fat emulsion than those of currently used fat emulsions (mean particle diameter ranging from 0.2 to 0.3 $\mu$m) can be achieved and phase separation in the fat emulsion caused by a difference in specific gravities can be effectively prevented.

A fat emulsion having a mean particle diameter of 0.17 $\mu$m or less can be prepared by adding one or more of the compounds selected from glycerol and glucose, followed by emulsification. The conventionally used emulsification method comprises adding a fat and an emulsifying agent to water, stirring the mixture to prepare a crude emulsion, and then emulsifying the crude emulsion by any commonly used means such as by a high pressure emulsification method. According to this method, it is difficult to obtain a fat emulsion having a mean particle diameter of 0.2 $\mu$m or less. The present inventors have found that glycerol and glucose have a specific capacity to make particles smaller. According to the above production method, a fat emulsion having a mean particle diameter of 0.17 $\mu$m or less can be prepared easily.

More illustratively, such a fat emulsion can be prepared, for example, by adding a fat source and an emulsifying agent to water, together with one or more compounds selected from glycerol and glucose, stirring the mixture to obtain a crude emulsion, and then emulsifying the crude emulsion by a conventional method such as by a high pressure emulsification method. When the emulsion is prepared by the high pressure emulsification method, the crude emulsion may be passed 5 to 50 times through a homogenizer such as a Manton-Gaulin homogenizer at a pressure condition of generally from 20 to 700 kg/cm$^2$.

In this instance, glycerol and/or glucose may be added at the time of the emulsification. For example, glycerol and/or glucose may be added to a crude emulsion prepared from a fat and an emulsifying agent.

The mean particle diameter of the thus prepared emulsion can be determined by a conventional method such as by a light scattering method.

In the above-described emulsion preparation method, a fat, an emulsifying agent and glycerol and/or glucose may be used in such amounts that the resulting fat emulsion consists of the fat in an amount of from 0.1 to 30% by w/v (unless otherwise noted, the term "%" as used hereinafter means w/v %), preferably from 1 to 20%, the emulsifying agent in an amount of from 0.01 to 10%, preferably from 0.05 to 5%, the glycerol and/or glucose in an amount of from 30 to 70%, preferably from 40 to 60%, and water in an appropriate amount.

Various types of sugars may be used as sugars contained in the infusion liquid included in the first compartment. Reducing sugars such as glucose, fructose, maltose and the like are particularly preferred. These reducing sugars may be used as a mixture of two or more. These reducing sugars may be mixed further with sorbitol, xylitol, glycerol and the like.

The first compartment contains at least vitamins C, $B_1$, $B_2$, A, D, E and K as vitamins.

These vitamins may be derivatives including vitamin C derivatives such as ascorbic acid, sodium ascorbate, ascorbic acid palmitate, ascorbic acid dipalmitate or magnesium salt of ascorbic acid phosphate, vitamin $B_1$ derivatives such as thiamine hydrochloride, prosultiamine or actothiamine, vitamin $B_2$ derivatives such as riboflavin phosphate, flavin mononucleotide or flavin adenine dinucleotide, vitamin A derivatives such as retinyl palmitate, vitamin D derivatives such as cholecalciferol ($D_3$) or ergocalciferol ($D_3$), vitamin E derivatives such as dl-$\alpha$-tocopherol, tocopherol acetate and vitamin K derivatives such as phytomenadione, menatetolenone or menadione.

The infusion liquid contained in the first compartment can be prepared by various methods. For example, sugars may be added to the fat emulsion prepared by the above-described method and may be added in advance at the time of preparation of the fat emulsion. With regard to the addition of vitamins (C, $B_1$, $B_2$, A, D, E, K), fat-soluble vitamins [vitamins (A, D, E, K)] can be dissolved in fat, in advance, and vitamins (C, $B_1$, $B_2$) can be dissolved in water, for injection, which is to be used to adjust the volume of the total liquid after preparation of the emulsion.

The composition of the infusion liquid containing a fat emulsion and a sugar in the first compartment can be varied depending on the concentration of the infusion liquid to be enclosed in the second compartment (that is, the infusion liquid containing amino acids, electrolytes and vitamins), the volumetric ratio of the liquids to be incorporated into the first and second compartments, and the like. A preferred example of the composition may consist of a fat in an amount of from approximately 0.1 to 30%, preferably from approximately 1 to 20%, more preferably from approximately 2 to 10%, an emulsifying agent in an amount of from approximately 0.01 to 10%, preferably from approximately 0.05 to 5%, more preferably from approximately 0.1 to 1%, sugars in an amount of from approximately 5 to 60%, preferably from approximately 7 to 40%, more preferably from approximately 10 to 30% and water in an appropriate amount.

The second compartment contains an infusion liquid comprising amino acids, electrolytes, at least vitamins ($B_6$, $B_{12}$) and folic acid.

Examples of the amino acids include various amino acids (essential and non-essential amino acids) which have been used in conventional amino acid infusion preparations for supplying the living body with nutrients, such as L-isoleucine, L-leucine, L-valine, L-lysine, L-methionine, L-phenylalanine, L-threonine, L-tryptophan, L-arginine, L-histidine, glycine, L-alanine, L-proline, L-aspartic acid, L-serine, L-tyrosine, L-glutamic acid, L-cysteine and the like. These amino acids may be used, not only as free amino acid forms, but also in various other forms which include for instance: inorganic acid salts such as L-lysine hydrochloride and the like; organic acid salts such as L-lysine acetate, L-lysine malate and the like; esters which can be hydrolyzed in vivo such as L-tyrosine methyl ester, L-methionine methyl ester, L-methionine ethyl ester and the like; N-substituted derivatives such as N-acetyl-L-tryptophan, N-acetyl-L-cysteine, N-acetyl-L-proline and the like; and dipeptides of the same or different amino acids such as L-tyrosyl-L-tyrosine, L-alanyl-L-tyrosine, L-arginyl-L-tyrosine, L-tyrosyl-L-arginine and the like.

Various types of water soluble salts which have been used in the prior art infusion preparations can be used as electrolytes, including chlorides, sulfates, acetates, gluconates, lactates and the like, water soluble salts of various inorganic components such as sodium, potassium, calcium, magnesium, zinc, iron, copper, manganese, iodine, phosphorus and the like, which are considered to be essential for the maintenance of biological functions and electrolyte balance in the body fluid. Hydrates of these water soluble salts may also be used.

In these electrolyte components, phosphoric esters of polyhydric alcohols or sugars or salts thereof may be used suitably as the source of phosphorus. Examples of phosphoric esters of polyhydric alcohols include glycerophosphoric acid, mannitol-1-phosphoric acid, sorbitol-1-phosphoric acid and the like. Examples of phosphoric esters of sugars include glucose-6-phosphoric acid, fructose-6-phosphoric acid and mannose-6-phosphoric acid and the like. As salts of these phosphoric esters, alkali metal salts such as sodium salt, potassium salt and the like may be used. Preferred phosphoric ester salts include a sodium salt and a potassium salt of glycerophosphoric acid.

The preferred electrolyte components include the following compounds:

Sodium: sodium chloride, sodium lactate, sodium acetate, sodium sulfate and sodium glycerophosphate;

Potassium: potassium chloride, potassium glycerophosphate, potassium sulfate, potassium acetate and potassium lactate;

Calcium: calcium gluconate, calcium chloride, calcium glycerophosphate, calcium lactate, calcium pantothenate and calcium acetate;

Magnesium: magnesium sulfate, magnesium chloride, magnesium glycerophosphate, magnesium acetate and magnesium lactate;

Phosphorus: potassium glycerophosphate, sodium glycerophosphate, magnesium glycerophosphate and calcium glycerophosphate; and Zinc: zinc sulfate, zinc chloride, zinc gluconate, zinc lactate and zinc acetate.

The second compartment contains, as vitamins, at least vitamins ($B_6$, $B_{12}$) and folic acid.

Derivatives of these vitamins may be used. Examples thereof include vitamin $B_6$ derivatives such as pyridoxine hydrochloride, pyridoxal phosphate or pyridoxamine phosphate and vitamin $B_{12}$ derivatives such as cyanocobalamin, hydroxocobalamin acetate or methylcobalamin.

The infusion liquid to be included in the second compartment can be prepared by various means, for example, by dissolving various amino acids and electrolytes in purified water such as water for injection. Vitamins ($B_6$, $B_{12}$) and folic acid can be added simultaneously at the time of dissolution of amino acids and electrolytes.

The composition of amino acids and electrolytes can be varied depending on the concentration of the infusion liquid to be enclosed in the first compartment (that is, an infusion liquid containing a fat emulsion, sugars and vitamins), the volumetric ratio of liquids to be injected into the first and second compartments and the like. A preferred example of the composition may consist of amino acids in a total amount of from approximately 1 to 15%, preferably from approximately 2 to 13%, more preferably from approximately 3 to 12% and, as electrolytes, approximately 50 to 180 mEq/l of sodium, approximately 40 to 135 mEq/l of potassium, approximately 10 to 50 mEq/l of calcium, approximately 5 to 30 mEq/l of magnesium, approximately 0 to 225 mEq/l of chlorine, approximately 3 to 40 mEq/l of phosphorus and 0 to 100 μmol/l of zinc, in addition to water in an amount necessary to give the above-described concentrations of each component.

Vitamins other than as described above including nicotinic acids, such as nicotinic acid or nicotinic-acid amide, pantothenic acids, such as sodium pantothenate, calcium pantothenate or pantothenol, and biotin may be included in either or both of the first and second compartments. Derivatives of these vitamins may be used. These vitamins can be added simultaneously at the time of dissolution of vitamins ($B_1$, $B_2$) when they are added in the first compartment. They can also be added simultaneously at the time of dissolution of vitamins ($B_6$, $B_{12}$) and folic acid, when added in the second compartment.

Amounts of the infusion liquids included in the first and second compartments, types, mixing ratios and concentrations of a fat emulsion, sugars, amino acids and electrolytes to be used in each infusion liquid can be adjusted depending on the use, the diseases and symptoms of the patient and other conditions. The following illustrates preferred compositions of the infusion preparation prepared by mixing the infusion liquids included in the first and second compartments:

| | |
|---|---|
| fat | 5–50 g/l |
| emulsifying agent | 0.5–10 g/l |
| sugar | 50–250 g/l |
| L-isoleucine | 0.5–5 g/l |
| L-leucine | 0.5–7 g/l |
| L-valine | 0.5–5 g/l |
| L-lysine | 0.5–7 g/l |
| L-methionine | 0.1–4 g/l |
| L-phenylalanine | 0.3–5 g/l |
| L-threonine | 0.3–5 g/l |
| L-tryptophan | 0.1–1 g/l |
| L-arginine | 0.3–7 g/l |
| L-histidine | 0.2–3 g/l |
| glycine | 0.2–3 g/l |
| L-alanine | 0.3–5 g/l |
| L-proline | 0.2–5 g/l |
| L-aspartic acid | 0.03–2 g/l |
| L-serine | 0.2–3 g/l |
| L-tyrosine | 0.03–0.5 g/l |
| L-glutamic acid | 0.03–2 g/l |
| L-cysteine | 0.03–1 g/l |
| sodium | 15–60 mEq/l |
| potassium | 10–50 mEq/l |
| calcium | 3–15 mEq/l |
| magnesium | 2–10 mEq/l |
| chlorine | 0–80 mEq/l |
| phosphorus | 1–15 mEq/l |
| zinc | 0–30 μmol/l |

Each vitamin mixture in the preparation of the present invention is preferably formulated, per dose, in an amount of 1 to 10 mg of vitamin $B_2$, 1 to 10 mg of vitamin $B_6$, 5 to 25 mg of pantothenic acids, 50 to 250 mg of vitamin C, 1 to 10 mg of vitamin $B_1$, 1 to 30 μg of vitamin $B_{12}$, 100 to 1000 μg of folic acid, 20 to 300 μg of biotin, 10 to 50 mg of nicotinic acid, 2000 to 5000 IU of vitamin A, 200 to 1000 IU of vitamin D, 5 to 20 IU of vitamin E and 0.2 to 10 mg of vitamin K.

The pH value of the infusion liquids contained in the first and second compartments is not particularly limited, but may be adjusted to from 5.0 to 8.0, preferably from 5.5 to 7.0, from the view point of safety to the living body. Especially, when a phosphoric ester of a polyhydric alcohol or a sugar or a salt of the ester is used as the source of phosphorus, precipitation can be effectively prevented even at a relatively high pH value.

Various acidic materials, preferably organic acids, can be used as agents for adjusting the pH of each of the above infusion liquids as long as they are physiologically acceptable. Examples of the organic acids include citric acid, gluconic acid, lactic acid, malic acid, maleic acid and malonic acid. Organic acids having chelating capacity against divalent metal ions are preferably used, with citric acid being particularly preferred.

In order to prevent coloring at the time of sterilization and during storage, an anti-coloring agent such as thioglycerol, dithiothreitol or the like may be added to the infusion liquids included in the first and second compartments, generally in an amount of about 1% or less. The anti-coloring agent may be added to either or both of the infusion liquids included in the first and second compartments.

In addition, the infusion liquid included in the first compartment may be further mixed with a buffer such as L-histidine, tris(hydroxymethyl)aminomethane or the like, generally in an amount of about 1% or less. Further, the infusion liquid included in the second compartment may be mixed with an antioxidant such as thioglycerol, sodium hydrogensulfite, or sodium sulfite, generally in an amount of approximately 0.001 to 0.1%.

The infusion liquids to be included in the first and second compartments may be sterilized in advance by heat sterilization or the like and then aseptically added, followed by sealing. Preferably, the respective infusion liquids are added in the first and second compartments (preferably in the presence of an inert gas), and the container is sealed and subjected to sterilization. The sterilization may be effected in a common way, for example, by a heat sterilization treatment such as high-pressure steam sterilization, hot water immersion sterilization, hot water shower sterilization or the like.

The container used in the present invention may be the container made of glass or plastic, such as polypropylene, polyethylene, ethylene-vinyl acetate copolymer, polyvinyl chloride, polyamide or polyester. Particularly, a flexible container made of plastic film or sheet is suitably used. As materials for the plastic film or sheet, the above-described materials or their laminated products are used. The container is preferably made of a material bearable with heat sterilization.

Considering stability during storage, the container having light-blocking property is preferably used. Examples thereof include a light-blocking bag and a ultraviolet light-blocking container.

BRIEF DESCRIPTION OF THE DRAWINGS

FIG. 3 is a cross-section of another example of a container of the present invention filled with infusion liquids.

DEFINITION OF SYMBOLS

1, 11 and 21: container, 2, 12 and 22: first compartment, 3, 13 and 23: second compartment, 4, 14 and 24: infusion liquid containing fat emulsion, sugars and vitamins for the first compartment, 5, 15 and 25: infusion liquid containing amino acids, electrolytes and vitamins for the second compartment, 6: a communicating means, 7, 16 and 28: a separation means and 8, 9, 10, 17, 18, 19, 26 and 27: ports.

BEST MODE FOR PRACTICE OF THE INVENTION

The present invention will be described in further detail based on the drawings showing the examples, but is not limited thereto.

Figure 1:
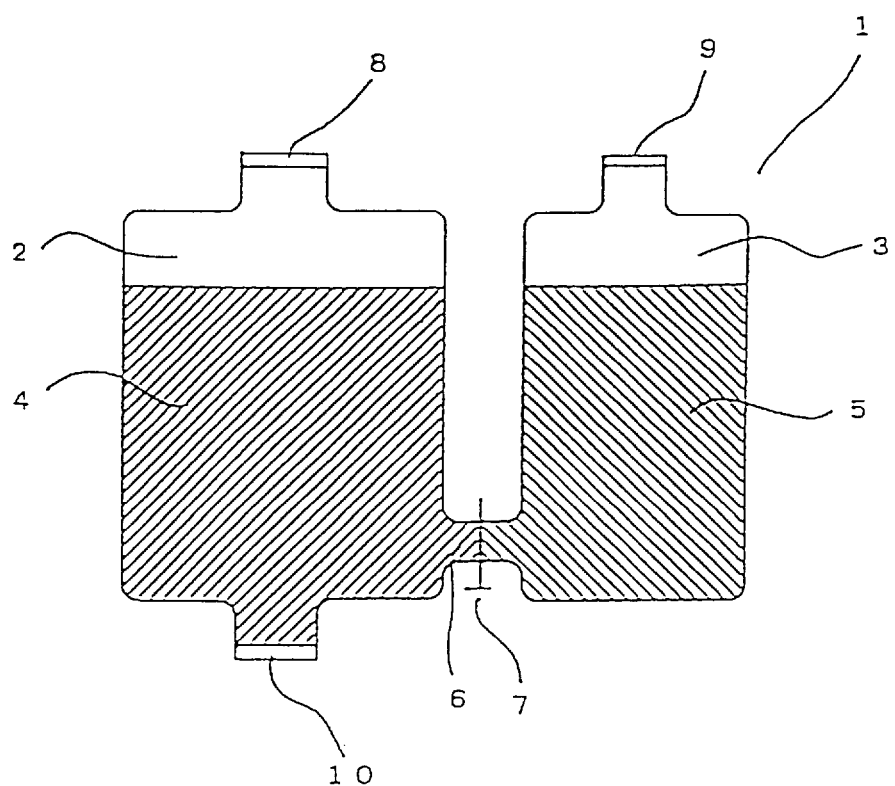
FIG. 1 is a cross-section of an example of a container of the present invention filled with infusion liquids.

FIG. 1 is a cross-sectional illustration showing an example of a container of the present invention filled with infusion liquids. In this figure, a container 1 is made of a material such as plastic film (including sheet, the same shall apply hereinafter) and has two compartments, that is, a first compartment 2 and a second compartment 3. An infusion liquid 4 containing a fat emulsion, sugars and vitamins (C, $B_1$, $B_2$, A, D, E, K) (hereinafter referred to as "vitamins" for the first compartment) is enclosed in the first compartment 2, and an infusion liquid 5 containing amino acids, electrolytes and vitamins ($B_6$, $B_{12}$) and folic acid (hereinafter referred to as "vitamins" for the second compartment) is enclosed in the second compartment 3. The first compartment 2 and the second compartment 3 are separated from each other by a separation means such as a pinch cock 7 attached to a communicating means 6, in order to prevent mixing of the infusion liquid 4 enclosed in the first compartment 2 with the infusion liquid 5 enclosed in the second compartment 3. In addition, the container 1 is equipped with a port 8 for use in the injection of the infusion liquid 4 into the first compartment 2, a port 9 for use in the injection of the infusion liquid 5 into the second compartment 3 and a port 10 for use in the ejection of a mixed preparation. If necessary, other agents can be injected through these ports.

This container filled with infusion liquids is obtained in the following manner. First, the communicating means 6 of the container 1 is shut off by a separation means such as the pinch cock 7 to separate the first compartment 2 and the second compartment 3 from each other, followed by the injection of an infusion liquid containing a fat emulsion, sugars and vitamins for the first compartment into the first compartment 2 through the port 8 and the injection of another infusion liquid containing amino acids, electrolytes and vitamins for the second compartment into the second compartment 3 through the port 9. In this instance, the infusion liquids to be injected into the first compartment 2 and/or the second compartment 3 may contain nicotinic acids, pantothenic acids and biotin, if required. It is preferable to carry out the injection of the infusion liquids 4 and 5 into the first compartment 2 and the second compartment 3 under a stream of an inert gas such as nitrogen, argon or the like. When the injection of the infusion liquids 4 and 5 into the first compartment 2 and the second compartment 3 is completed, the ports 8 and 9 are sealed and the resulting container is sterilized to obtain the infusion liquids-enclosed container of FIG. 1. The sterilization may be effected in any common way, for example, by heat sterilization such as high-pressure steam sterilization, hot water immersion sterilization, hot water shower sterilization or the like. When a plastic container is used as in this case, it is preferable to carry out its sterilization in an atmosphere which does not contain a detectable amount of oxygen.

The thus-obtained infusion liquids-enclosed container of the present invention can be stored as it is. An infusion preparation containing a fat emulsion, sugars, amino acids, electrolytes and vitamins can be aseptically prepared at the time of use by removing the pinch cock 7 to allow the first compartment 2 and the second compartment 3 to communicate with each other and mixing the infusion liquids 4 and 5 enclosed in the respective compartments. Thereafter, the thus mixed infusion preparation is ejected aseptically from the port 8 through a tube (not shown in the figure) and administered to the living body.

Figure 2:
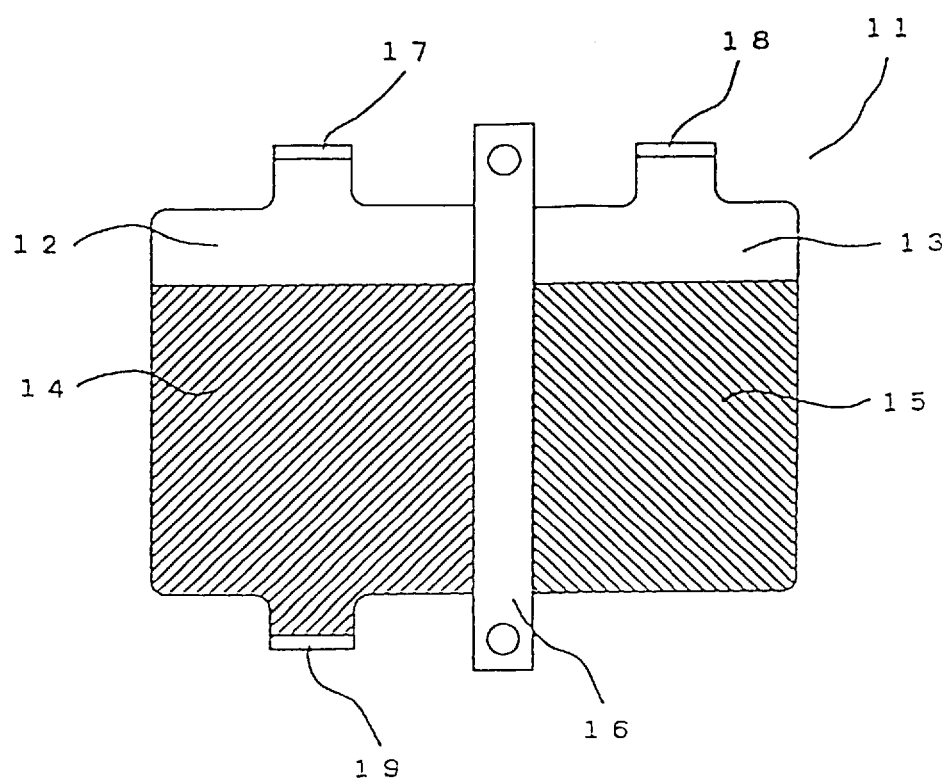
FIG. 2 is a cross-section of another example of a container of the present invention filled with infusion liquids.

FIG. 2 is a cross-sectional illustration showing another example of a container of the present invention filled with infusion liquids. In this figure, a container 11 is made of a material such as plastic film and has two compartments, that is, a first compartment 12 and a second compartment 13 which are separated from each other by a large screw cock 16. An infusion liquid 14 containing a fat emulsion, sugars and vitamins for the first compartment is enclosed in the first compartment 12 and another infusion liquid 15 containing amino acids, electrolytes and vitamins for the second compartment is enclosed in the second compartment 13. Since the first compartment 12 and the second compartment 13 are separated from each other by the screw cock 16, the infusion liquid 14 enclosed in the first compartment 12 cannot be mixed with the infusion liquid 15 enclosed in the second compartment 13. In addition, the container 11 is equipped with a port 17 for use in the injection of the infusion liquid 14 into the first compartment 12, a port 18 for use in the injection of the infusion liquid 15 into the second compartment 13 and a port 19 for use in the ejection of mixed preparation. If necessary, other agents can be injected through these ports. The production process and use of the container filled with infusion liquids shown in FIG. 2 are substantially the same as those of the container filled with the infusion liquids shown in FIG. 1.

FIG. 3 is a cross-sectional illustration showing another example of a container of the present invention filled with infusion liquids. In this figure, a container 11 is made of a material such as plastic film and has two compartments, that is, a first compartment 22 and a second compartment 23 which are separated from each other by a separation part 28 formed by heat fusion. The separation part 28 becomes open by applying external power. The first compartment 22 contains an infusion liquid 24 containing a fat emulsion, sugars and vitamins for the first compartment and the second compartment 23 contains another infusion liquid 25 containing amino acids, electrolytes and vitamins for the second compartment. Since the first compartment 22 and the second compartment 23 are separated from each other by the separation part 28, the infusion liquid 24 enclosed in the first compartment 22 cannot be mixed with the infusion liquid 25 enclosed in the second compartment 23. In addition, the container 21 is equipped with a port 26 for use in the injection of the infusion liquid 24 into the first compartment 22 and a port 27 for use in the injection of the infusion liquid 25 into the second compartment 23. If necessary, other agents can be injected through these ports. Ejection of the infusion preparation can be effected through the port 26 or 27. The container filled with infusion liquids shown in FIG. 3 can be produced by injecting an infusion liquid into either of the first compartment 22 or the second compartment 23 followed by sealing, reversing the container, and injecting another infusion liquid into the other compartment. The sterilization method and use of the container are substantially the same as those of the container filled with the infusion liquids shown in FIG. 1, but admixture of the infusion liquids included in the first compartment 22 and the second compartment 23 is carried out by allowing the separation part 28 to be open by applying external power upon use.

The infusion liquids-enclosed containers shown in FIGS. 1, 2 and 3 are only an aspect of the present invention and are not to be construed as limiting the invention. Shape, size and the like of the container can be changed at will. The main body of the infusion liquids-enclosed container may be equipped with a hanging part at an appropriate position for hanging the container on a common hook. The separation means is also not to be limited to the above examples. For example, in FIG. 1, a clip may be used instead of the pinch cock 7, or the first and second compartments may be separated from each other by installing a ball cock inside the communicating means 6.

In order to prevent denaturation of the enclosed infusion liquids in the container, the container filled with infusion liquids according to the present invention may be wrapped with an oxygen-impermeable film material. Examples of such oxygen-impermeable film materials include: three layer laminate films in which an ethylene-vinyl alcohol copolymer film, a polyvinyl alcohol film, a polyvinylidene chloride film or the like is used as an intermediate layer (for example, a laminate film which comprises outer layers of a polyester film, a stretched nylon film, a stretched polypropylene film and the like and an internal layer of an unstretched polypropylene film); laminate films having an aluminum layer (for example, a laminate film composed of polyester film-aluminum layer-unstretched polypropylene film); and laminate films having an inorganic material-deposited film (for example, a laminate film composed of polyester film-silicon-deposited film-unstretched polypropylene film, stretched nylon film-silicon-deposited film-unstretched polypropylene film, polyester film-aluminum-deposited film-unstretched polypropylene film or alumina-deposited polyester film-polyvinylidene chloride film-unstretched polypropylene film).

An oxygen scavenger such as Ageless (trade name) may be put between the wrapping material and the container, or vacuum packaging or inert gas (nitrogen for example)-charged packaging may be effected in the usual way.

The infusion preparation containing a fat emulsion, sugars, amino acids, electrolytes and vitamins, obtained by mixing the infusion liquids included in the first and second compartments, has an excellent shelf life, is free from precipitation, denaturation, coloring and the like, and can be stored for about one week. The infusion preparation may be administered to a patient by intravenous injection, as it is, or after being diluted with water, if necessary by mixing it with other drugs and the like. It may also be used in a dosage form for oral or rectal administration and the like.

The present invention will be illustrated in more detail based on the following production examples, but is not to be construed as being limited to these examples.

PRODUCTION EXAMPLE 1

(1) Preparation of infusion liquid containing fat emulsion, sugars and vitamins Five thousand IU of vitamin A palmitate, 200 IU of vitamin $D_2$, 140 mg of vitamin E (α-tocopherol) and 200 μg of vitamin $K_1$ were dissolved in 66 g of soybean oil and 9.5 g of egg yolk phospholipid and 500 g of glucose were added to water. These were preliminarily emulsified using a mixer. After adding water in which 80 mg of sodium ascorbate, 3.5 mg of thiamine nitrate, 5.4 mg of riboflavin phosphate and 20 mg of pantothenol had been dissolved, the total volume was adjusted to 1,000 ml to obtain a crude emulsion. The resulting emulsion was emulsified using a Manton-Gaulin homogenizer (15M-8TA, manufactured by Gaulin) until the mean particle diameter became 0.17 μm or less. Water was added to 500 ml of the thus obtained emulsion to make the total volume 1,000 ml. The composition of the thus-obtained infusion preparation is shown in Table 1.

TABLE 1

| Component | Amount (g) |
| --- | --- |
| Soybean oil | 33 |
| Egg yolk phospholipid | 4.75 |

TABLE 1-continued

| Component | Amount (g) |
| --- | --- |
| Glucose | 250 |
| Vitamin A palmitate | 2500 IU |
| Vitamin $D_2$ | 100 IU |
| Vitamin E | 70 mg |
| Vitamin $K_1$ | 100 μg |
| Na ascorbate (C) | 40 mg |
| Thiamine nitrate ($B_1$) | 1.75 mg |
| Riboflavin phosphate ($B_2$) | 2.7 mg |
| Pantothenol | 10 mg |
| Distilled water for injection | amount necessary for making total volume 1,000 ml |

(2) Preparation of infusion liquid containing amino acids, electrolytes and vitamins Amino acids, electrolytes and vitamins shown in Table 2, Table 3 and Table 4 were added to and dissolved in water for injection which was maintained at about 80° C. under a stream of nitrogen gas so as to give the respective concentrations. The pH value was adjusted to pH 6.2 with citric acid.

TABLE 2

| Component | Concentration (per liter) |
| --- | --- |
| L-isoleucine | 8.000 g |
| L-leucine | 14.000 g |
| L-valine | 8.000 g |
| L-lysine.HCl | 10.000 g |
| L-methionine | 4.000 g |
| L-phenylalanine | 8.000 g |
| L-threonine | 6.000 g |
| L-tryptophan | 1.200 g |
| L-arginine | 10.500 g |
| L-histidine | 5.000 g |
| glycine | 5.300 g |
| L-alanine | 8.500 g |
| L-proline | 6.000 g |
| L-aspartic acid | 1.500 g |
| L-serine | 3.000 g |
| L-tyrosine | 0.500 g |
| L-glutamic acid | 1.500 g |
| N-acetyl-L-cysteine | 1.100 g |

TABLE 3

| Component | Concentration (per liter) |
| --- | --- |
| sodium chloride | 1.949 g |
| potassium chloride | 4.302 g |
| magnesium sulfate.$7H_2O$ | 2.054 g |
| calcium gluconate.$H_2O$ | 6.352 g |
| dipotassium glycerophosphate (50%) | 8.016 g |
| sodium acetate.$3H_2O$ | 11.340 g |
| zinc sulfate.$7H_2O$ | 9.585 mg |

TABLE 4

| Component | Concentration (per liter) |
| --- | --- |
| pyridoxine hydrochloride ($B_6$) | 2.7 mg |
| cyanocobalamin ($B_{12}$) | 2.2 μg |
| folic acid | 0.22 mg |
| nicotinic-acid amide | 10 mg |
| biotin | 0.33 mg |

(3) Preparation of infusion liquids-enclosed container

A polypropylene container having a structure as shown in FIG. 1 was used. After closing the communicating means 6 with the pinch cock 7, 600 ml of the infusion liquid containing a fat emulsion, sugars and vitamins obtained in the above (1) was injected into the first compartment 2 from the port 8 with nitrogen gas charging, subsequently sealing the port 8. In the same manner, 300 ml of the infusion liquid containing amino acids, electrolytes and vitamins obtained above was injected into the second compartment 3 from the port 9 with nitrogen gas charging, subsequently sealing the port 9. The thus-prepared container 1 in which each infusion liquid was enclosed was sterilized by autoclaving at 115° C. for 30 minutes, followed by cooling to room temperature. Thus, the container filled with infusion liquids according to the present invention was obtained.

(4) Stability test of the infusion preparation prepared using the container filled with infusion liquids of the present invention In the infusion liquids-enclosed container as obtained in the above (3), the pinch cock 7 was removed from the communicating means 6, and the infusion liquids in the first compartment 2 and the second compartment 3 were mixed thoroughly through the communicating means 6 to obtain an infusion preparation containing a fat emulsion, sugars, amino acids, electrolytes and vitamins. The composition of the thus-obtained infusion preparation is shown in Table 5.

The thus obtained infusion preparation was preserved at 25° C. for one week and the changes of appearance, mean particle diameter and turbidity were measured. The results are shown in Table 6. Separately, 300 ml of water for injection was injected into the second compartment 3, sterilization was carried out in the same manner, and each liquid was mixed. The resulting mixture was used as a control. The mean particle diameter of the fat emulsion was measured by the light scattering method, and turbidity was measured in terms of absorbance at 620 nm (1-cm cell).

As shown in Table 6, no change was observed in appearance, mean particle diameter or turbidity. The results reveal that the infusion preparation prepared using the infusion liquids-enclosed container of the present invention shows high stability.

TABLE 5

| Composition (per 1 liter) | Infusion preparation of Production Example 1 |
|---|---|
| Fat | |
| soybean oil | 22.00 g |
| egg yolk phospholipid | 3.17 g |
| Sugar | |
| glucose | 166.07 g |
| Amino acids | |
| L-isoleucine | 2.67 g |
| L-leucine | 4.67 g |
| L-valine | 2.67 g |
| L-lysine.HCl | 3.33 g |
| L-methionine | 1.33 g |
| L-phenylalanine | 2.67 g |
| L-threonine | 2.00 g |
| L-tryptophan | 0.40 g |
| L-arginine | 3.50 g |
| L-histidine | 1.67 g |

TABLE 5-continued

| Composition (per 1 liter) | Infusion preparation of Production Example 1 |
|---|---|
| glycine | 1.77 g |
| L-alanine | 2.83 g |
| L-proline | 2.00 g |
| L-aspartic acid | 0.50 g |
| L-serine | 1.00 g |
| L-tyrosine | 0.17 g |
| L-glutamic acid | 0.50 g |
| N-acetyl-L-cysteine | 0.37 g |
| Electrolytes | |
| sodium | 38.89 mEq |
| potassium | 30.00 mEq |
| calcium | 9.44 mEq |
| magnesium | 5.56 mEq |
| chlorine | 48.60 mEq |
| phosphorus | 5.37 mEq |
| zinc | 11.11 μmol |
| Vitamins | |
| vitamin A palmitate | 2500 IU |
| vitamin $D_2$ | 100 IU |
| vitamin E | 70 mg |
| vitamin $K_1$ | 100 μg |
| Na ascorbate (C) | 40 mg |
| thiamine nitrate ($B_1$) | 1.7 mg |
| riboflavin phosphate ($B_2$) | 2.7 mg |
| pantothenol | 10 mg |
| pyridoxine hydrochloride ($B_6$) | 2.7 mg |
| cyanocobalamin ($B_{12}$) | 2.2 mg |
| folic acid | 0.22 mg |
| nicotinic-acid amide | 10 mg |
| biotin | 0.33 mg |
| Others | |
| citric acid | 1.401 g |

TABLE 6

| | Storage time | | | |
|---|---|---|---|---|
| Test item | Immediately after mixing | After 24 hr. | After 48 hr. | After 1 week |
| Inventive preparation | | | | |
| Appearance | No change | No change | No change | No change |
| Mean particle diameter | 0.15 μm | 0.16 μm | 0.16 μm | 0.16 μm |
| Turbidity | 0.034 | 0.034 | 0.030 | 0.040 |
| Control | | | | |
| Appearance | No change | No change | No change | No change |
| Mean particle diameter | 0.16 μm | 0.16 μm | 0.16 μm | 0.16 μm |
| Turbidity | 0.034 | 0.031 | 0.031 | 0.036 |

TEST EXAMPLE

(1) Method

Relationship between the composition of vitamins in each compartment and stability of the infusion preparation was examined. According to Table 7, the infusion liquid for the first compartment and the infusion liquid for the second compartment were prepared and stored at 40° C. for three months in the dark. Thereafter, the residual rate of each vitamin was compared. The results are shown in Table 8.

For comparison, the same test was carried out in the case where fat-soluble vitamins (A, D, E, K) were injected into the first compartment and water-soluble vitamins (B, C, nicotinic-acid amide, pantothenol, folic acid and biotin) were injected into the second compartment.

TABLE 7

| Component | Comparison 1 | Comparison 2 | Invention |
|---|---|---|---|
| First compartment (fat + sugar) | | | |
| vitamin A palmitate | 2500 IU | ← | ← |
| vitamin $D_2$ | 100 IU | ← | ← |
| vitamin E | 70 mg | ← | ← |
| vitamin $K_1$ | 100 µg | ← | ← |
| Na ascorbate (C) | — | 40 mg | ← |
| thiamine nitrate ($B_1$) | — | 1.7 mg | ← |
| riboflavin phosphate ($B_2$) | — | 2.7 mg | ← |
| pyridoxine hydrochloride ($B_6$) | — | 2.7 mg | — |
| nicotinic-acid amide | — | — | 10 mg |
| Second compartment (amino acids + electrolytes) | | | |
| Na ascorbate (C) | 40 mg | — | — |
| thiamine nitrate ($B_1$) | 1.7 mg | — | — |
| riboflavin phosphate ($B_2$) | 2.7 mg | — | — |
| pyridoxine hydrochloride ($B_6$) | 2.7 mg | — | — |
| cyanocobalamin ($B_{12}$) | 2.2 µg | ← | ← |
| nicotinic-acid amide | 10 mg | ← | ← |
| pantothenol | 10 mg | ← | ← |
| folic acid | 0.22 mg | ← | ← |
| biotin | 0.33 mg | ← | ← |

In the table, an arrow means the same as left.

TABLE 8

| Component | Comparison 1 | Comparison 2 | Invention |
|---|---|---|---|
| vitamin A palmitate | 98 | ← | ← |
| vitamin $D_2$ | 80 | ← | ← |
| vitamin E | 99 | ← | ← |
| vitamin $K_1$ | 98 | ← | ← |
| Na ascorbate (C) | 64 | 95 | 100 |
| thiamine nitrate ($B_1$) | 59 | 82 | 84 |
| riboflavin phosphate ($B_2$) | 92 | 100 | 100 |
| pyridoxine hydrochloride ($B_6$) | 75 | 85 | 99 |
| cyanocobalamin ($B_{12}$) | 48 | 93 | 97 |
| nicotinic-acid amide | 96 | 100 | 100 |
| pantothenol | 91 | 94 | 96 |
| folic acid | 72 | 100 | 100 |
| biotin | 85 | 94 | 98 |

In the table, an arrow means the same as left.

(2) Results

As shown in Table 8, various vitamins are stably maintained according to the composition of the present invention.

On the other hand, when vitamin $B_6$ is added to the first compartment (fat+sugar), its stability is lower than that in the composition of the present invention. Thus, such a composition is not considered desirable.

In the system in which fat-soluble vitamins are added in the first compartment and water-soluble vitamins are added in the second compartment, stability of water-soluble vitamins, particularly vitamins C, $B_1$, $B_6$, $B_{12}$, folic acid and biotin, becomes worse and such a composition is not also considered desirable. One of ordinary skill in the art would easily expect the composition of vitamins of Comparison 1. However, a good effect cannot be always obtained from this composition. Therefore, it is a remarkable achievement that a stable composition is obtained by a specific combination of vitamins.

INDUSTRIAL APPLICABILITY

As described above, according to the present invention, an infusion liquid containing a fat emulsion, sugars and vitamins and another infusion liquid containing amino acids, electrolytes and vitamins are respectively included in separate compartments and the infusion preparation containing sugars, amino acids, electrolytes, a fat emulsion and vitamins can be prepared by only removing a separation means upon use. In addition, the thus obtained infusion preparation is highly stable without suffering from precipitation, phase separation, denaturation and like problems. Accordingly, the present invention provides an infusion preparation excellent in stability and safety. Further, since it is not necessary to mix a fat emulsion, sugars, amino acids, electrolytes and vitamins, the operation can be simplified and contamination with microorganisms at the time of admixture can be prevented.

Particularly, as a result of investigation of the composition of vitamins, more specifically the composition of vitamins to be added in the above-described first compartment (fat+sugar) and the composition of vitamins to be added in the above-described second compartment (amino acid+electrolyte) and improvement of a means of addition, an infusion preparation can be prepared in which vitamins are stably maintained without affecting stability of sugars, amino acids, electrolytes and a fat emulsion. Therefore, the present invention improves an infusion preparation containing sugars, amino acids, electrolytes and a fat emulsion and provides a more complete high calorie infusion preparation with saving the operation of adding vitamins upon clinical use.

We claim:

1. A container, filled with infusion liquids, comprising two compartments which are separated from each other by a separation means and containing an infusion liquid comprising a fat emulsion, sugar, vitamin C, vitamin $B_1$, vitamin $B_2$, vitamin A, vitamin D, vitamin E, vitamin K in a first compartment and an infusion liquid comprising amino acid, electrolyte, vitamin $B_6$, vitamin $B_{12}$ and folic acid in a second compartment.

2. The container filled with infusion liquids as claimed in claim 1, wherein at least one of the first and second compartments contains pantothenic acid, nicotinic acid and biotin.

3. A container filled with an infusion liquid comprising a container and therein an infusion liquid comprising a fat emulsion, sugar, vitamin C, vitamin $B_1$, vitamin $B_2$, vitamin A, vitamin D, vitamin E, vitamin K, amino acid, electrolyte, vitamin $B_6$, vitamin $B_{12}$ and folic acid, wherein said container filled with an infusion liquid is made by removing the separation means from a container, filled with infusion liquids, comprising two compartments which are separated from each other by a separation means and containing an infusion liquid comprising a fat emulsion, sugar, vitamin C, vitamin $B_1$, vitamin $B_2$, vitamin A, vitamin D, vitamin E, vitamin K in a first compartment, and an infusion liquid comprising amino acid, electrolyte, vitamin $B_6$, vitamin $B_{12}$ and folic acid in a second compartment and mixing the infusion liquid of said first compartment with the infusion liquid of said second compartment.

* * * * *